(12) United States Patent
Braun

(10) Patent No.: US 6,503,282 B1
(45) Date of Patent: Jan. 7, 2003

(54) MEANS AND METHOD FOR DYING KERATINIC FIBERS

(75) Inventor: Hans-Juergen Braun, Ueberstorf (CH)

(73) Assignee: Wella Aktiengesellschaft, Darmstadt (DE)

( * ) Notice: Subject to any disclaimer, the term of this patent is extended or adjusted under 35 U.S.C. 154(b) by 0 days.

(21) Appl. No.: 09/913,553

(22) PCT Filed: Dec. 16, 2000

(86) PCT No.: PCT/EP00/12847
§ 371 (c)(1),
(2), (4) Date: Aug. 15, 2001

(87) PCT Pub. No.: WO01/51019
PCT Pub. Date: Jul. 19, 2001

(30) Foreign Application Priority Data

Jan. 7, 2000 (DE) .......................... 100 00 460

(51) Int. Cl.⁷ ................................. A61K 7/13
(52) U.S. Cl. .................. 8/405; 8/401; 8/405; 8/406; 8/408; 564/99; 564/443
(58) Field of Search ............... 8/401, 404, 405, 8/406, 408; 564/99, 443

(56) References Cited

U.S. PATENT DOCUMENTS

| | | | | |
|---|---|---|---|---|
| 3,617,167 A | * | 11/1971 | Berth et al. .................... | 8/10.2 |
| 3,634,013 A | * | 1/1972 | Benshein ......................... | 8/11 |
| 3,909,190 A | * | 9/1975 | Saygin .......................... | 8/10.1 |
| 4,259,261 A | | 3/1981 | Bugaut et al. ................. | 564/99 |
| 4,329,504 A | | 5/1982 | Bugaut et al. ............... | 564/443 |
| 5,534,267 A | * | 7/1996 | Neunhoeffer et al. ........ | 424/701 |
| 5,980,584 A | | 11/1999 | Lim et al. ...................... | 8/408 |
| 6,251,145 B1 | * | 6/2001 | De La Mettrie et al. ....... | 8/407 |
| 6,273,920 B1 | * | 8/2001 | De La Mettrie et al. ....... | 8/401 |
| 6,306,180 B1 | * | 10/2001 | Audousset ..................... | 8/407 |

FOREIGN PATENT DOCUMENTS

| | | |
|---|---|---|
| DE | 197 57 510 A | 5/1999 |
| WO | 99 29285 A | 6/1999 |
| WO | 99 66890 A | 12/1999 |

OTHER PUBLICATIONS

Database WPI, Section Ch, Week 198031, Derwent Publications Ltd., London, GB; An 1980–54659C, XP002163850 Bristol–Myers Co: 3–(2,4–Diamoniphenoxy)–1,2 . . . ) Zusammenfassung and Research Disclosure, BD. 195, NR. 013, Jul. 10, 1980.

* cited by examiner

Primary Examiner—Yogendra N. Gupta
Assistant Examiner—Eisa Elhilo
(74) Attorney, Agent, or Firm—Michael J. Striker

(57) ABSTRACT

Composition for coloring keratin fibers based on a developer-coupler combination characterized in that it contains as the coupler 3-(2,4-diaminophenoxy)-1-propanol and as the developer a p-phenylenediamine derivative monosubstituted on the benzene ring and having general formula (I)

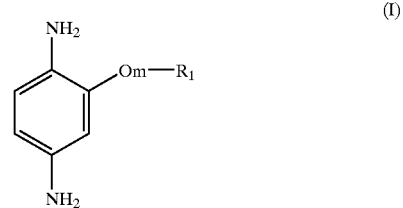

and/or
a 4,5-diamino-1H-pyrazole derivative of general formula (II)

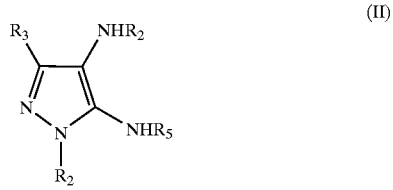

and/or
a p-aminophenol derivative of general formula (III)

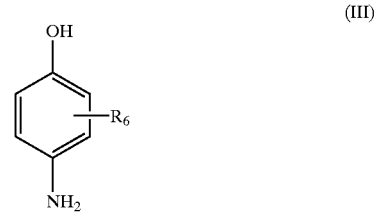

as well as a method for the oxidative coloring of hair, and the use of said composition.

11 Claims, No Drawings

MEANS AND METHOD FOR DYING KERATINIC FIBERS

BACKGROUND OF THE INVENTION

The present invention concerns a composition for coloring keratin fibers, particularly human hair, said composition containing 3-(2,4-diaminophenoxy)-1-propanol and at least one p-phenylenediamine derivative, 4,5-diamino-1H-pyrazole derivative or p-aminophenol derivative, and a method for coloring keratin fibers.

Oxidation dyes have attained essential importance in the field of hair coloring. The color is created by reaction of certain developers with certain couplers in the presence of an oxidant.

Oxidation dyes intended to be used for coloring human hair must meet numerous special requirements. Said dyes must be toxicologically and dermatologically harmless and non-sensitizing and they must produce colors of the desired intensity.

The hair colors must remain stable for at least four to six weeks. It is also expected that the hair colorations will remain stable when other cosmetic treatments are applied, such as shampooing or hair restyling. The hair colors should also be resistant to external effects such as light and weather as well as to perspiration and mechanical abrasion.

It is also necessary to be able to create a wide range of different color shades by combining appropriate developers and couplers.

The preparation of stable blue and reddish color shades presents a particular problem. Blue-coloring hair dye couplers together with yellow and red color components are needed for producing natural-looking hair colorations. Fashionable reddish hair colors, on the other hand, are created by use of an excess of the red color component.

The stability of the hair colors in both the blue and the red range, however, still leaves much to be desired, particularly as regards the action of organic acids and perspiration.

SUMMARY OF THE INVENTION

Surprisingly, we have now found that with a combination consisting of the coupler 3-(2,4-diamino-phenoxy)-1-propanol and at least one developer selected from the group consisting of certain p-phenylenediamine derivatives, 4,5-diamino-1H-pyrazole derivatives and p-aminophenol derivatives, it is possible to prepare hair colorants which, compared to the prior art, present substantially improved resistance to organic acids and perspiration besides outstanding washing and light fastness.

The preparation of 3-(2,4-diaminophenoxy)-1-propanol dihydrochloride and the use thereof in hair colorants are known from U.S. Pat. Nos. 4,259,261 and 4,329,504.

The object of the present invention is a composition for coloring keratin fibers, particularly human hair, based on a developer-coupler combination, characterized in that it contains as the coupler 3-(2,4-diaminophenoxy)-1-propanol and as the developer a p-phenylenediamine derivative monosubstituted on the benzene ring and having general formula (I)

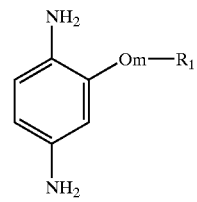

(I)

wherein m equals 0 or 1 and $R_1$ is a straight-chain or branched $C_3$–$C_6$-alkyl group, a straight-chain or branched monohydroxy-$(C_1$–$C_6)$-alkyl group or a polyhydroxy-$(C_2$–$C_6)$-alkyl group, a straight-chain or branched mono-$(C_2$–$C_6)$-alkoxy-$(C_2$–$C_6)$-alkyl group or poly-$(C_2$–$C_6)$-alkoxy-$(C_2$–$C_6)$-alkyl group or a carbocyclic or heterocyclic, substituted or unsubstituted aromatic compound; and/or a 4,5-diamino-1H-pyrazole derivative of general formula (II)

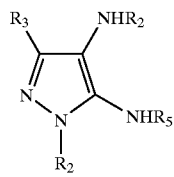

(II)

wherein $R_2$, $R_4$ and $R_6$ independently of each other denote a hydrogen atom or a straight-chain or branched $C_2$–$C_6$-alkyl group, a straight-chain or branched monohydroxy-$(C_1$–$C_6)$-alkyl group or a polyhydroxy-$(C_2$–$C_6)$-alkyl group or an unsubstituted benzyl group or a benzyl group substituted on the benzene ring, and $R_3$ denotes a straight-chain or branched $C_1$–$C_6$-alkyl group, a straight-chain or branched monohydroxy-$(C_1$–$C_6)$-alkyl group or polyhydroxy-$(C_2$–$C_6)$-alkyl group, a straight-chain or branched mono-$(C_2$–$C_6)$-alkoxy-$(C_2$–$C_6)$-alkyl group or poly-$(C_2$–$C_6)$-alkoxy-$(C_2$–$C_6)$-alkyl group, or a carbocyclic or heterocyclic, substituted or unsubstituted aromatic compound; and/or a p-aminophenol derivative of general formula (III)

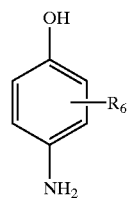

(III)

wherein $R_6$ is a straight-chain or branched $C_1$–$C_6$-alkyl group, a straight-chain or branched monohydroxy-$(C_1$–$C_6)$-alkyl group or polyhydroxy-$(C_2$–$C_6)$-alkyl group, a straight-chain or branched mono-$(C_2$–$C_6)$-alkoxy-$(C_2$–$C_6)$-alkyl group or poly-$(C_2$–$C_6)$-alkoxy-$(C_2$–$C_6)$-alkyl group, a straight-chain or branched amino-$(C_2$–$C_6)$-alkyl group or a carbocyclic or heterocyclic, substituted or unsubstituted aromatic compound.

DESCRIPTION OF THE PREFERRED EMBODIMENTS

Preferred p-phenylenediamine derivatives of formula (I) are 2-propyl-p-phenylenediamine, 2-(hydroxymethyl)-p- phenylenediamine, 2-(1-hydroxyethyl)-p-phenylenediamine, 2-(2-hydroxyethyl)-p-phenylenediamine, 2-(3-hydroxypropyl)-p-phenylenediamine, 2-(1,2-dihydroxyethyl)-p-phenylenediamine, 2-(methoxymethyl)-p-phenylenediamine, 2-(2-methoxyethyl)-p-phenylenediamine, 2-(2-hydroxyethoxy)-p-phenylenediamine, 2,5-diaminobiphenyl, 2-(2-thienyl)-p-phenylenediamine, 2-(3-thienyl)-p-phenylenediamine and 3-(2,5-diaminophenyl)pyridine.

Preferred pyrazole derivatives of formula (II) are 4,5-diamino-1-methyl-1H-pyrazole, 4,5-diamino-1-(2-hydroxyethyl)-1H-pyrazole, 4,5-diamino-1-(1-methylethyl)-1H-pyrazole, 4,5-diamino-1-(phenylmethyl)-1H-pyrazole, 4,5-diamino-1-[(4-methylphenyl)methyl]-1H-pyrazole, 4,5-diamino-1-(2-hydroxyethyl)-3-methyl-1H-pyrazole and 4,5-diamino-1-methyl-3-phenyl-1H-pyrazole.

Preferred p-aminophenol derivatives of formula (III) are 3-methyl-p-aminophenol, 2-aminomethyl-p-aminophenol, 2-hydroxymethyl-p-aminophenol, 3-hydroxymethyl-p-aminophenol, 2-phenyl-p-aminophenol, 2-(2-thienyl)-p-aminophenol, 2-(3-thienyl)-p-aminophenol, 3-(2-thienyl)-p-aminophenol and 3-(3-thienyl)-p-aminophenol.

To complete the coloring treatment and to create special color effects, other developers and/or couplers as well as direct dyes can be added to the combinations of the invention.

Suitable developers are, for example, the following compounds: 1,4-diaminobenzene, 1,4-diamino-2-methylbenzene, 1,4-diamino-2,6-dimethylbenzene, 2,5-diamino-1,3-diethylbenzene, 1,4-diamino-2,5-dimethylbenzene, 1,4-diamino-2,3-dimethylbenzene, 2-chloro-1,4-diaminobenzene, 1-(aminomethyl)-2,5-diaminobenzene, 2-[2-(acetylamino)ethoxy]-1,4-diaminobenzene, 4-phenylaminoaniline, 4-dimethylaminoaniline, 4-(dipropylamino)aniline, 4-diethylaminoaniline, 4-[ethyl(2-hydroxyethyl)amino]aniline, 4-[di(2-hydroxyethyl)amino]aniline, 4-[di(2-hydroxyethyl)amino]-2-methylaniline, 4-[(2-methoxyethyl)amino]aniline, 4-[(3-hydroxypropyl)amino]aniline, 4-[(2,3-dihydroxypropyl)amino]aniline, 1,3-bis-[(4-aminophenyl)(2-hydroxyethyl)amino]-2-propanol, 1,4-di[(4-aminophenyl)amino]butane, 1,8-bis-(2,5-diaminophenoxy)-3,6-dioxaoctane, 4-aminophenol, 4-amino-3-fluorophenol, 4-methylaminophenol, 4-amino-2-(aminomethyl)phenol, 4-amino-2-(hydroxymethyl)phenol, 4-amino-2-fluorophenol, 4-amino-2-[(2-hydroxyethyl)amino]methylphenol, 4-amino-2-methylphenol, 4-amino-2-(methoxymethyl)phenol, 4-amino-2-(2-hydroxyethyl)phenol, 5-aminosalicylic acid, 2,5-diaminopyridine, 2,4,5,6-tetraaminopyrimidine and 2,5,6-triamino-4(1H)-pyrimidone.

Suitable couplers are, for example, the following compounds: 2,6-diaminopyridine, 2-amino-4-[(2-hydroxyethyl)amino]anisole, 2,4-diamino-1-fluoro-5-methylbenzene, 2,4-diamino-1-methoxy-5-methylbenzene, 2,4-diamino-1-ethoxy-5-methylbenzene, 2,4-diamino-1-(2-hydroxyethoxy)-5-methylbenzene, 2,4-di[(2-hydroxyethyl)amino]-1,5-dimethoxybenzene, 2,3-diamino-6-methoxypyridine, 3-amino-6-methoxy-2-(methylamino)pyridine, 2,6-diamino-3,5-dimethoxypyridine, 3,5-diamino-2,6-dimethoxypyridine, 1,3-diaminobenzene, 2,4-diamino-1-(2-hydroxyethoxy)benzene, 2,4-diamino-1,5-di(2-hydroxyethoxy)benzene, 1-(2-aminoethoxy)-2,4-diaminobenzene, 2-amino-(2-hydroxyethoxy)-4-methylaminobenzene, 2,4-diaminophenoxyacetic acid, 3-[di(2-hydroxyethyl)amino]aniline, 4-amino-2-di[(2-hydroxyethyl)amino]-1-ethoxybenzene, 5-methyl-2-(1-methylethyl)phenol, 3-[(2-hydroxyethyl)amino]aniline, 3-[(2-aminoethyl)amino]aniline, 1,3-di(2,4-diaminophenoxy)propane, di(2,4-diaminophenoxy)methane, 1,3-diamino-2,4-dimethoxybenzene, 2,6-bis(2-hydroxyethyl)aminotoluene, 4-hydroxyindole, 3-dimethylaminophenol, 3-diethylaminophenol, 5-amino-2-methylphenol, 5-amino-4-fluoro-2-methylphenol, 5-amino-4-methoxy-2-methylphenol, 5-amino-4-ethoxy-2-methylphenol, 3-amino-2,4-dichlorophenol, 5-amino-2,4-dichlorophenol, 3-amino-2-methylphenol, 3-amino-2-chloro-6-methylphenol, 3-aminophenol, 2-[(3-hydroxyphenyl)amino]acetamide, 5-[(2-hydroxyethyl)amino]-2-methylphenol, 3-[(2-hydroxyethyl)amino]phenol, 3-[(2-methoxyethyl)amino]phenol, 5-amino-2-ethylphenol, 2-(4-amino-2-hydroxyphenoxy)ethanol, 5-[(3-hydroxypropyl)amino]-2-methylphenol, 3-[(2,3-dihydroxypropyl)amino]-2-methylphenol, 3-[(2-hydroxyethyl)amino]-2-methylphenol, 2-amino-3-hydroxypyridine, 5-amino-4-chloro-2-methyl-phenol, 1-naphthol, 1,5-dihydroxynaphthalene, 1,7-dihydroxynaphthalene, 2,3-dihydroxynaphthalene, 2,7-dihydroxynaphthalene, 2-methyl-1-naphthol acetate, 1,3-dihydroxybenzene, 1-chloro-2,4-dihydroxybenzene, 2-chloro-1,3-dihydroxybenzene, 1,2-dichloro-3,5-dihydroxy-4-methylbenzene, 1,5-dichloro-2,4-dihydroxybenzene, 1,3-dihydroxy-2-methylbenzene, 3,4-methylenedioxyphenol, 3,4-methylenedioxyaniline, 5-[(2-hydroxyethyl)amino]-1,3-benzodioxole, 6-bromo-1-hydroxy-3,4-methylenedioxybenzene, 3,4-diaminobenzoic acid, 3,4-dihydroxy-6-hydroxy-1,4(H)-benzoxazine, 6-amino-3,4-dihydro-1,4(2H)-benzoxazine, 3-methyl-1-phenyl-5-pyrazolone, 5,6-dihydroxyindole, 5,6-dihydroxyindoline, 5-hydroxyindole, 6-hydroxyindole, 7-hydroxyindole and 2,3-indolinedione.

In addition, the colorant of the invention can also contain other colorant components such as, for example, 2-aminophenol, 2-amino-6-methylphenol or 2-amino-5-methylphenol.

Suitable direct dyes are, for example, the following compounds: 4-[(4'aminophenyl)(-(4'-imino-2",5"-cyclohexadien-1"-ylidene)methyl]-2-methylaminobenzene monohydrochloride (C.I.[1] 42 510), 4-[(4'-amino-3'-methylphenyl)-(4"-imino-3"-methyl-2",5"-cyclohexadien-1"-ylidene)methyl]-2-methylaminobenzene monohydrochloride, (C.I. 42 520), 4-[(2'-hydroxyethyl)amino]nitrotoluene, 2-amino-4,6-dinitrophenol, 2-amino-5-[(2'-hydroxyethyl)amino]nitrobenzene, 2-chloro-6-(ethylamino)-4-nitrophenol, 4-chloro-N-(2-hydroxyethyl)-2-nitroaniline, 5-chloro-2-hydroxy-4-nitroaniline, 2-amino-4-chloro-6-nitrophenol, 1-[(2'-ureidoethyl)amino]-4-nitrobenzene, sodium 6-[(4'-aminophenyl)azo]-5-hydroxynaphthalene 1-sulfonate, (C.I. 14 805), 1,4-diaminoanthraquinone and 1,4,5,8-tetraaminoanthraquinone.

[1] C.I.=Color Index-Translator

Particularly preferred hair colorants are those containing one of the following developer-coupler combinations of the invention:

3-(2,4-diaminophenoxy)-1-propanol and 2-(1-hydroxyethyl)-p-phenylenediamine;

3-(2,4-diaminophenoxy)-1-propanol and 2-(2-hydroxyethyl)-p-phenylenediamine;

3-(2,4-diaminophenoxy)-1-propanol and 2-propyl-p-phenylenediamine;

3-(2,4-diaminophenoxy)-1-propanol and 2-(3-hydroxypropyl)-p-phenylenediamine;

3-(2,4-diaminophenoxy)-1-propanol and 2-(1,2-dihydroxyethyl)-p-phenylenediamine;

3-(2,4-diaminophenoxy)-1-propanol and 2-(methoxymethyl)-p-phenylenediamine;

3-(2,4-diaminophenoxy)-1-propanol and 2-(2-methoxyethyl)-p-phenylenediamine;

3-(2,4-diaminophenoxy)-1-propanol and 2-(2-hydroxyethoxy)-p-phenylenediamine;
3-(2,4-diaminophenoxy)-1-propanol and 2,5-diaminobiphenyl;
3-(2,4-diaminophenoxy)-1-propanol and 2-(2-thienyl)-p-phenylenediamine;
3-(2,4-diaminophenoxy)-1-propanol and 2-(3-thienyl)-p-phenylenediamine;
3-(2,4-diaminophenoxy)-1-propanol and 3-(2,5-diaminophenyl)pyridine;
3-(2,4-diaminophenoxy)-1-propanol and 4,5-diamino-1-methyl-1H-pyrazole;
3-(2,4-diaminophenoxy)-1-propanol and 4,5-diamino-1-(2-hydroxyethyl)-1H-pyrazole;
3-(2,4-diaminophenoxy)-1-propanol and 4,5-diamino-1-(1-methylethyl)-1H-pyrazole
3-(2,4-diaminophenoxy)-1-propanol and 4,5-diamino-1-(phenylmethyl)-1H-pyrazole;
3-(2,4-diaminophenoxy)-1-propanol and 4,5-diamino-1-[(4-methylphenyl)methyl]-1H-pyrazole;
3-(2,4-diaminophenoxy)-1-propanol and 4,5-diamino-1-(2-hydroxyethyl)-3-methyl-1H-pyrazole;
3-(2,4-diaminophenoxy)-1-propanol and 4,5-diamino-1-methyl-3-phenyl-1H-pyrazole;
3-(2,4-diaminophenoxy)-1-propanol and 3-methyl-p-aminophenol;
3-(2,4-diaminophenoxy)-1-propanol and 2-aminomethyl-p-aminophenol;
3-(2,4-diaminophenoxy)-1-propanol and 2-phenyl-p-aminophenol;
3-(2,4-diaminophenoxy)-1-propanol and 2-(2-thienyl)-p-aminophenol;
3-(2,4-diaminophenoxy)-1-propanol and 2-(3-thienyl)-p-aminophenol;
3-(2,4-diaminophenoxy)-1-propanol and 3-(2-thienyl)-p-aminophenol;
3-(2,4-diaminophenoxy)-1-propanol and 3-(3-thienyl)-p-aminophenol;
3-(2,4-diaminophenoxy)-1-propanol and 2-(2-hydroxyethyl)-p-phenylenediamine and 3-methyl-p-aminophenol;
3-(2,4-diaminophenoxy)-1-propanol and 2-(2-hydroxyethyl)-p-phenylenediamine and 4,5-diamino-1-(2-hydroxyethyl)-1H-pyrazole;
3-(2,4-diaminophenoxy)-1-propanol and 2-methyl-p-phenylenediamine and 3-methyl-p-aminophenol;
3-(2,4-diaminophenoxy)-1-propanol and 2-methyl-p-phenylenediamine and 4,5-diamino-1-(2-hydroxyethyl)-1H-pyrazole;
3-3-(2,4-diaminophenoxy)-1-propanol and 2-methoxymethyl-p-phenylenediamine and 3-methyl-p-aminophenol;
3-(2,4-diaminophenoxy)-1-propanol and 2-methoxymethyl-p-phenylenediamine and 4,5-diamino-1-(2-hydroxyethyl)-1H-pyrazole;
3-(2,4-diaminophenoxy)-1-propanol and 2-(2-thienyl)-p-phenylenediamine and 3-methyl-p-aminophenol;
3-(2,4-diaminophenoxy)-1-propanol and 2-(2-thienyl)-p-phenylenediamine and 4,5-diamino-1-(2-hydroxyethyl)-1H-pyrazole;
3-(2,4-diaminophenoxy)-1-propanol and 2,5-diamino-1,1'-biphenyl and 3-methyl-p-aminophenol;
3-(2,4-diaminophenoxy)-1-propanol and 2,5-diamino-1,1'-biphenyl and 4,5-diamino-1-(2-hydroxyethyl)-1H-pyrazole;
3-(2,4-diaminophenoxy)-1-propanol and 2-(2-hydroxyethoxy)-p-phenylenediamine and 3-methyl-p-aminophenol;
3-(2,4-diaminophenoxy)-1-propanol and 2-(2-hydroxyethoxy)-p-phenylenediamine and 4,5-diamino-1-(2-hydroxyethyl)-1H-pyrazole;
3-(2,4-diaminophenoxy)-1-propanol and N,N-bis(2-hydroxyethyl)-p-phenylenediamine and 4,5-diamino-1-(2-hydroxyethyl)-1H-pyrazole;
3-(2,4-diaminophenoxy)-1-propanol and p-phenylenediamine and 4,5-diamino-1-(2-hydroxyethyl)-1H-pyrazole.

The aforesaid combinations according to the invention can also contain one or more additional couplers, particularly resorcinol, 2-methylresorcinol, 3-aminophenol, 5-amino-2-methylphenol, 3-amino-2-chloro-6-methylphenol or 1-naphthol.

Naturally, the couplers and developers and the other colorant components, if they are bases, can also be used in the form of their physiologically tolerable salts with organic or inorganic acids, for example hydrochloric acid or sulfuric acid, or—if they contain aromatic OH groups—in the form of salts with bases, for example as alkali metal phenoxides.

The colorant of the invention contains each of 3-(2,4-diaminophenoxy)-1-propanol and the compounds of formulas (I) to (III) in an amount ranging from about 0.01 to 5 wt. % and preferably from 0.01 to 3.0 wt. %, the total amount of developers and couplers in the composition of the invention being about 0.1 to 10 wt. %.

Moreover, if the colorants are used for coloring hair, they can contain other common cosmetic additives, for example antioxidants such as ascorbic acid, thioglycolic acid or sodium sulfite, or perfume oils, complexing agents, wetting agents, emulsifiers, thickeners and hair-care agents.

The colorant of the invention can be formulated, for example, as a solution, particularly an aqueous or aqueous-alcoholic solution, or as a cream, gel, aerosol foam or emulsion, the use in the form of a cream, gel or emulsion being particularly preferred. Such compositions consist of a mixture of the dye components and the additives commonly used for such formulations.

Common additives to solutions, creams, emulsions or gels are, for example, solvents such as water, lower aliphatic alcohols, for example ethanol, propanol or isopropanol, and glycerol or glycols such as 1,2-propylene glycol, furthermore wetting agents or emulsifiers belonging to the class of anionic, cationic, amphoteric or nonionic surface-active agents, for example fatty alcohol sulfates, ethoxylated fatty alcohol sulfates, alkyl sulfonates, alkylbenzene sulfonates, alkyltrimethylammonium salts, alkylbetaines, ethoxylated fatty alcohols, ethoxylated nonylphenols, fatty acid alkanolamides and ethoxylated fatty esters, furthermore thickeners such as the higher fatty alcohols, starch, cellulose derivatives, petrolatum, paraffin oil and fatty acids, moreover hair-care agents such as cationic resins, lanolin derivatives, cholesterol, pantothenic acid and betaine. The said components are employed in the amounts commonly used for these purposes, for example the wetting agents and emulsifiers at a concentration of about 0.5 to 30 wt. %, the thickeners in an amount of about 0.1 to 25 wt. % and the hair-care agents at a concentration of about 0.1 to 5.0 wt. %.

Depending on the composition, the colorant of the invention can be weakly acidic, neutral or alkaline. In particular, it has a pH of 6.8 to 11.5, the adjustment requiring the addition of a base preferably being done with ammonia. Organic amines such as, for example, monoethanolamine and triethanolamine, or inorganic bases such as sodium hydroxide and potassium hydroxide, can also be used. Suitable for pH adjustment requiring the addition of an acid are inorganic or organic acids, for example phosphoric, acetic, citric or tartaric acid.

For oxidative coloring of hair, the afore-described colorant is mixed with an oxidant just before use, and an amount of this mixture sufficient for the hair-coloring treatment, generally about 60 to 200 grams, depending on the body of the hair, is applied to the hair.

Suitable oxidants for developing the hair coloration are primarily hydrogen peroxide or its products of addition to urea, melamine, sodium borate or sodium carbonate in the form of a 3–12%, preferably 6%, aqueous solution, but also atmospheric oxygen. When a 6% hydrogen peroxide solution is used as the oxidant, the weight ratio of hair colorant to oxidant is from 5:1 to 1:2, but preferably 1:1. A larger amount of oxidant is used primarily at high dye concentrations in the hair colorant or when pronounced bleaching of the hair is desired at the same time. The mixture is allowed to act on the hair at 15 to 50° C. for about 10 to 45 minutes, preferably 30 minutes, after which the hair is rinsed with water and dried. Optionally, after this rinsing, the hair is washed with a shampoo and optionally post-rinsed with a weak organic acid, for example citric acid or tartaric acid. The hair is then dried.

The hair colorant of the invention is characterized by outstanding physiological tolerability and gives hair colorations with excellent color fastness, particularly light fastness, wash fastness and fastness to rubbing, as well as resistance to the effects of acids and perspiration. We have also found that combinations containing the sulfate salt of 3-(2,4-diaminophenoxy)-1-propanol give unusually stable hair colorations. As regards their coloring properties, the hair colorants of the invention give, depending on the composition of the dye components, a wide range of different color shades ranging from blond to brown to purple, violet, blue and black. Such color shades are characterized by an unusual color intensity. The very good dyeing properties of the hair colorants of the present invention also manifest themselves in that with said colorants it is possible to color readily and with good hiding grayed hair which previously has not been chemically damaged.

The following examples illustrate the object of the invention without limiting the scope of the invention.

EXAMPLES

EXAMPLE OF A SYNTHESIS

Example 1

Preparation of 3-(2,4-diaminophenoxy)-1-propanol sulfate 10 g of 2,4-dinitro-1-(3-hydroxypropoxy)benzene in 100 mL of ethanol was hydrogenated using 1 g of 10% palladium catalyst at 5 bar hydrogen pressure. After 6 hours, the catalyst was removed under inert gas, and the resulting solution was stirred into 50 mL of tetrahydrofuran/3 mL of concd. sulfuric acid. The resulting precipitate was filtered off and suspended in tetrahydrofuran at room temperature for 1 hour. Suction-filtration and drying gave 6.5 g of a colorless product melting at 190–192° C.

$^1$H-NMR (DMSO): 1.83 ppm (dt, $^3J_{HH}$=6.1 Hz, $^3J_{HH}$=6.4 Hz, 2H); 3.57 ppm (t, $^3J_{HH}$=6.1 Hz, 2H); 3.99 ppm (t, $^3J_{HH}$=6.4 Hz, 2H); 6.45 ppm (dd, $^3J_{HH}$=8.4 Hz, $^4J_{HH}$=2.6 Hz, 1H); 6.58 ppm (d, $^4J_{HH}$=2.6 Hz, 1H); 6.82 ppm (d, $^3J_{HH}$=8.4 Hz, 1H); 9.4 ppm (s, broad, 3H).

EXAMPLES OF HAIR COLORANTS

Examples 2–21

Hair Colorant Solutions with a Basic pH

| | |
|---|---|
| 10.00 g | of ethanol |
| 10.00 g | of sodium lauryl ether sulfate, 28% solution in water |
| 10.00 g | of ammonia, 25% aqueous solution |
| 0.30 g | of ascorbic acid |
| 0.70 g | of 3-(2,4-diaminophenoxy)-1-propanol sulfate |
| X g | of developer as per Table 1 |
| to 100.00 g | demineralized water |

Before use, 10 grams of the foregoing hair colorant solution was mixed with 10 grams of a 6% aqueous hydrogen peroxide solution. An appropriate amount of the resulting oxidation hair dye, which had a pH between 9 and 11, was then applied to bleached hair. After an exposure time of 30 min at 40° C., the hair was washed with a color-protection shampoo, rinsed and dried. The resulting color shades and color intensities are shown in Table 1,

TABLE 1

Hair Coloring Examples 2–21

| Example No. | Developer X | X, g | Shade |
|---|---|---|---|
| 2 | 2-propyl-p-phenylenediamine | 0.38 | blue |
| 3 | 2-(hydroxymethyl)-p-phenylenediamine | 0.35 | dark-blue |
| 4 | 2-(1-hydroxyethyl)-p-phenylenediamine | 0.38 | violet-blue |
| 5 | 2-(2-hydroxyethyl) p-phenylenediamine | 0.38 | dark-blue |
| 6 | 2-(1,2-dihydroxyethyl)-p-phenylenediamine | 0.42 | blue |
| 7 | 2-(methoxymethyl)-p-phenylenediamine | 0.42 | violet-blue |
| 8 | 2-(2-hydroxyethoxy)-p-phenylenediamine | 0.42 | bluish black |
| 9 | 2-(3-hydroxypropyl)-p-phenylenediamine | 0.42 | blue |
| 10 | 2-(2-thienyl)-p-phenylenediamine | 0.48 | greenish blue |
| 11 | 4,5-diamino-1-methyl-1H-pyrazole | 0.28 | purplish red |
| 12 | 4,5-diamino-1-(2-hydroxyethyl)-1H-pyrazole | 0.36 | purplish red |
| 13 | 4,5-diamino-1-(1-methylethyl)-1H-pyrazole | 0.35 | purplish red |
| 14 | 4,5-diamino-1-(phenylmethyl)-1H-pyrazole | 0.47 | purplish red |
| 15 | 4,5-diamino-1-(4-methylphenyl)methyl-1H-pyrazole | 0.51 | purplish red |
| 16 | 4,5-diamino-1-(2-hydroxyethyl)-3-methyl-1H-pyrazole | 0.39 | violet |
| 17 | 4,5-diamino-1-methyl-3-phenyl-1H-pyrazole | 0.47 | bluish violet |
| 18 | 2-methyl-4-aminophenol | 0.31 | purple |
| 19 | 3-methyl-4-aminophenol | 0.31 | purplish red |
| 20 | 2-hydroxymethyl-4-aminophenol | 0.35 | pinkish red |
| 21 | 3-hydroxymethyl-4-aminophenol | 0.35 | pink |

Examples 22–31

Hair Colorant Cream, Basic

| | |
|---|---|
| 15.00 g | of cetylstearyl alcohol, 50/50 |
| 5.00 g | of glycerol monostearate |
| 10.00 g | of sodium lauryl ether sulfate, 28% aqueous solution |
| 0.30 g | of sodium sulfite |
| 5.00 g | of ammonia, 25% aqueous solution |
| X g | of dye, as per Table 3 |
| to 100.00 g | demineralized water |

Immediately before use, the foregoing colorant cream was mixed with 100 grams of a 6% aqueous hydrogen peroxide solution. An appropriate amount of the resulting oxidation hair colorant was then applied to medium-blond natural hair. After an exposure time of 30 min at 40° C., the hair was rinsed with lukewarm water and then dried.

TABLE 2

Coloring Results for Examples 22–31

| Example No. | Color |
|---|---|
| 22 | brownish black |
| 23 | bluish black |
| 24 | reddish brown |
| 25 | bluish black |
| 26 | garnet red |
| 27 | reddish brown |
| 28 | violet-black |
| 29 | brown |
| 30 | violet-blue |
| 31 | dark brown |

The resulting color shade was then measured in the Lab system with a Minolta color-measuring instrument, model Chromameter II, and compared with the corresponding color values for the colored hair before the acid treatment. Here the L value stands for luminosity (namely, the lower the L value, the higher is the color intensity), and the a-value is a measure of the red content (namely, the higher the a-value, the higher is the red content). The b-value is a measure of the blue content of the color, the blue content being the higher the more negative the b-value.

As a measure of the stability of the color, the total color change $\Delta E$ of the hair strands caused by the acid treatment was determined by the following formula:

$$\Delta E = \sqrt{(L_0 - L_s)^2 + (a_0 - a_s)^2 + (b_0 - b_s)^2}$$

TABLE 3

Hair Coloring Examples 22–31 (all amounts are in grams/100 g of colorant)

| Dye/Example No. | 22 | 23 | 24 | 25 | 26 | 27 | 28 | 29 | 30 | 31 |
|---|---|---|---|---|---|---|---|---|---|---|
| 3-(2,4-Diaminophenoxy)-1-propanol sulfate | 1.6 | | 0.02 | | | 0.1 | 0.6 | 0.6 | 0.3 | 0.05 |
| 3-(2,4-Diaminophenoxy)-1-propanol dihydrochloride | | 1.4 | | 0.8 | 0.6 | | | | | |
| 2-Methoxymethyl-p-phenylenediamine dihydrochloride | | 0.1 | | 1.0 | | | | | | |
| 2-Methyl-p-phenylenediamine sulfate | 0.1 | 1.0 | | | | | | | | 1.0 |
| 2-(2-Hydroxyethyl)-p-phenylenediamine sulfate | | 0.1 | | | | | 1.0 | | | |
| 2-Aminomethyl-p-phenylenediamine dihydrochloride | | 0.05 | | | | 0.3 | | 1.5 | | |
| 4-Amino-3-methylphenol | | 0.3 | | | | 0.3 | | | | |
| 4,5-Diamino-1-[(4-methylphenyl)methyl]-1H-pyrazole sulfate | 1.5 | | | | | | | 0.05 | 0.2 | |
| 4,5-Diamino-1-(2-hydroxyethyl)-1H-pyrazole sulfate | 0.05 | | 0.1 | | 0.6 | | 0.3 | | | |
| 4,5-Diamino-1-(1-methylethyl)-1H-pyrazole sulfate | 0.03 | | | | | 0.02 | | | | |
| 5-[(2-Hydroxyethyl)amino]-2-methoxyaniline sulfate | 0.01 | | 0.02 | | | | | | | |
| 1-(2-Hydroxyethylamino)-3,4-methylenedioxybenzene | 0.2 | | | | | | | | | |
| Resorcinol | | 0.3 | | 0.2 | | | | 0.6 | | 0.3 |
| 2-Methylresorcinol | 0.05 | 0.05 | | | | 0.1 | | 0.1 | | 0.2 |
| 5-Amino-2-methylphenol | 0.05 | 0.05 | | 0.2 | | | | | | |
| 3-Aminophenol | 0.3 | 0.06 | | 0.1 | | | 0.3 | 0.1 | | 0.1 |
| 2-Amino-6-chloro-4-nitrophenol | 0.1 | | 0.05 | | | | | 0.2 | | |
| 2-Chloro-6-(ethylamino)-4-nitrophenol | 0.1 | | 0.05 | | | | | 0.1 | | |
| p-Phenylenediamine | | 0.5 | | | | 0.05 | | | | |
| 2-(1-Hydroxyethyl)-p-phenylenediamine | | 0.02 | | 0.3 | | | | | | |
| 2-(2,4-Diaminophenoxy)ethanol sulfate | | 0.05 | 0.05 | | 0.05 | | | | | |
| N,N-Bis(2-hydroxyethyl)-p-phenylenediamine sulfate | 0.1 | | | 0.2 | | 0.05 | | | 1.0 | |
| 4-Aminophenol | | 0.02 | | | | | | | | |
| 2,4-Diamino-1-fluoro-5-methylbenzene sulfate | | | | | 0.05 | | | | | |
| 3-Amino-6-methoxy-2-(methylamino)pyridine.2 HCl | | 0.1 | | | | | | | | |
| N-[3-(Dimethylamino)phenyl]urea | | | 0.05 | | 0.1 | | | 0.01 | | |
| 5-Amino-6-chloro-o-cresol | | 0.1 | 0.05 | | 0.05 | 0.2 | 0.1 | | | |
| 1-Naphthol | 0.08 | | | 0.1 | | 0.05 | | | 0.6 | |
| 1-Acetoxy-2-methylnaphthalene | 0.02 | | | | | | | | | |
| 4-Chlororesorcinol | | 0.1 | | | | | | 0.02 | | 0.2 |
| Sesamol | | 0.05 | | | | | | 0.02 | | 0.1 |
| 6-Amino-m-cresol | 0.05 | | | 0.03 | | 0.05 | | | | 0.02 |
| 2,6-Diamino-3-pyridin-3-ylazopyridine | 0.01 | | | | | | | 0.02 | | |

Example 32

Comparative Examples

To demonstrate the improved acid resistance/perspiration resistance of the colors obtained with the colorants of the invention, hair colored with a colorant according to the invention (Examples A–D) and hair colored with a colorant not according to the invention (Examples A'–D') were treated for 48 hours at 37° C. with a solution of 10% sodium chloride, 1% dipotassium hydrogen phosphate and 0.25% histidine, adjusted to pH 3.2 with lactic acid. The hair was then washed with water and dried.

Hair Colorants

| | |
|---|---|
| 10.00 g | of ethanol |
| 10.00 g | of sodium lauryl ether sulfate, 28% aqueous solution |
| 10.00 g | of ammonia, 25% aqueous solution |
| 0.30 g | of ascorbic acid |
| 2.5 mmol | of coupler as per Table 4 |
| 2.5 mmol | of developer as per Table 4 |
| to 100.00 g | demineralized water |

TABLE 4

| Example | Coupler | Developer |
|---|---|---|
| A (as per invention) | 3-(2,4-diaminophenoxy)-1-propanol dihydrochloride | 2-(2-hydroxyethyl-p-phenylenediamine sulfate |
| A' | 2-(2,4-diaminophenoxy)-ethanol dihydrochloride | 2-(2-hydroxyethyl)-p-phenylenediamine sulfate |
| B (as per invention) | 3-(2,4-diaminophenoxy)-1-propanol dihydrochloride | 4,5-diamino-1-(2-hydroxyethyl)-1H-pyrazole sulfate |
| B' | 2-(2,4-diaminophenoxy)-ethanol dihydrochloride | 4,5-diamino-1-(2-hydroxyethyl)-1H-pyrazole sulfate |
| C (as per invention) | 3-(2,4-diaminophenoxy)-1-propanol sulfate | 2-(2-hydroxyethyl)-p-phenylenediamine sulfate |
| C' | 2-(2,4-diaminophenoxy)-ethanol sulfate | 2-(2-hydroxyethyl)-p-phenylenediamine sulfate |
| D (as per invention) | 3-(2,4-diaminophenoxy)-1-propanol sulfate | 4,5-diamino-1-(2-hydroxyethyl)-1H-pyrazole sulfate |
| D' | 2-(2,4-diaminophenoxy)-ethanol sulfate | 4,5-diamino-1-(2-hydroxyethyl)-1H-pyrazole sulfate |

TABLE 5

| | Color Measurements | | | | | |
|---|---|---|---|---|---|---|
| Example | $L_0$ | $a_0$ | $b_0$ | $L_s$ | $a_s$ | $b_s$ | $\Delta E$ |
| A | 17.16 | +3.73 | −8.88 | 25.02 | +6.52 | −5.52 | 9.0 |
| $A^f$ | 16.01 | +2.30 | −5.20 | 24.40 | +7.45 | −5.12 | 9.8 |
| B | 19.67 | +24.27 | +4.52 | 28.00 | +25.69 | +5.51 | 8.5 |
| $B^f$ | 19.47 | +23.84 | +4.13 | 33.25 | +29.40 | +5.21 | 14.9 |
| C | 15.66 | +1.66 | −3.48 | 21.80 | +6.12 | −2.58 | 7.6 |
| $C^f$ | 17.03 | +2.96 | −6.86 | 27.01 | +6.21 | −3.55 | 11.0 |
| D | 19.72 | +24.21 | +4.44 | 25.57 | +27.65 | +4.84 | 6.8 |
| $D^f$ | 20.45 | +29.76 | +5.31 | 30.85 | +30.02 | +3.75 | 10.5 |

Unless otherwise indicated, all percentages given are by weight.

What is claimed is:

1. A composition for coloring keratin fibers based on a developer-coupler combination, said composition comprising at least one developer compound and 3-(2,4-diaminophenoxy)-1-propanol, said 3-(2,4-diaminophenoxy)-1-propanol acting as a coupler;

wherein said at least one developer compound is selected from the group consisting of p-phenylenediamine derivatives of formula I:

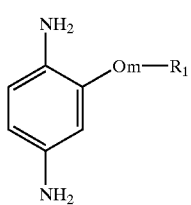

(I)

wherein m=0 or 1 and $R_1$ is a straight-chain $C_3$- to $C_6$-alkyl group, branched $C_3$- to $C_6$-alkyl group, a straight-chain $C_1$- to $C_6$-alkyl group, branched monohydroxy-$(C_1-C_6)$-alkyl group, or a polyhydroxy-$(C_2-C_6)$-alkyl group, a straight-chain mono-$(C_2-C_6)$-alkoxy-$(C_2-C_6)$-alkyl group, branched mono-$(C_2-C_6)$-alkoxy-$(C_2-C_6)$-alkyl group, poly-$(C_2-C_6)$-alkoxy-$(C_2-C_6)$-alkyl group, a carbocyclic or heterocyclic, substituted or unsubstituted aromatic compound;

4,5-diamino-1H-pyrazole compounds of formula II:

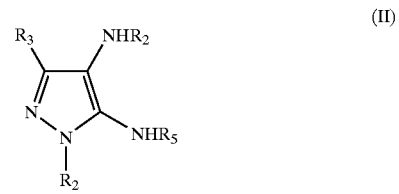

(II)

wherein $R_2$, $R_4$ and $R_5$, independently of each other, denote a hydrogen atom, a straight-chain $C_1$- to $C_6$-alkyl group branched $C_1$- to $C_6$-alkyl group, a straight-chain monohydroxy-$(C_1-C_6)$-alkyl group branched monohydroxy-$(C_1-C_6)$-alkyl group, a polyhydroxy-$(C_2-C_6)$-alkyl group, an unsubstituted benzyl group, a substituted benzyl group substituted on a benzene ring thereof, and $R_3$ denotes a straight-chain $C_1$- to $C_6$-alkyl group, branched $C_1$- to $C_6$-alkyl group, a straight-chain monohydroxy-$(C_1-C_6)$-alkyl group branched monohydroxy-$(C_1-C_6)$-alkyl group, a polyhydroxy-$(C_2-C_6)$-alkyl group, a straight-chain mono-$(C_2-C_6)$-alkoxy-$(C_2-C_6)$-alkyl group branched mono-$(C_2-C_6)$-alkoxy-$(C_2-C_6)$-alkyl group, poly-$(C_2-C_6)$-alkoxy-$(C_2-C_6)$-alkyl group, a carbocyclic, heterocyclic, substituted aromatic compound, unsubstituted aromatic compound, or wherein $R_2$ denotes a methyl group, an isopropyl group, a 2-hydroxyethyl group, a benzyl group, or a 4-methylbenzyl group, when $R_3$, $R_4$ and $R_5$ are each said hydrogen atom; and p-aminophenol derivatives of formula III:

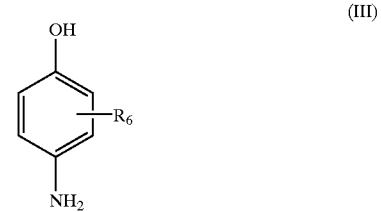

(III)

wherein $R_6$ is a straight-chain $C_1$- to $C_6$-alkyl group branched $C_1$- to $C_6$-alkyl group, a straight-chain monohydroxy-(C1–C6)-alkyl group branched monohydroxy-$(C_1-C_6)$-alkyl group, a polyhydroxy-$(C_2-C_6)$-alkyl group, a straight-chain mono-$(C_2-C_6)$-alkoxy-$(C_2-C_6)$-alkyl group branched mono-$(C_2-C_6)$-alkoxy-$(C_2-C_6)$-alkyl group, poly-$(C_2-C_6)$-alkoxy-$(C_2-C_6)$-alkyl group, a carbocyclic, heterocyclic, substituted or unsubstituted aromatic compound.

2. The composition as defined in claim 1, wherein said p-phenylenediamine derivatives are selected from the group consisting of 2-propyl-p-phenylenediamine, 2-(hydroxymethyl)-p-phenylenediamine, 2-(1-hydroxyethyl)-p-phenylenediamine, 2-(2-hydroxyethyl)-p-phenylenediamine, 2-(3-hydroxyethyl)-p-phenylenediamine, 2-(1,2-dihydroxyethyl)-p-phenylenediamine, 2-(methoxymethyl)-p-phenylenediamine, 2-(2-methoxyethyl)-p-phenylenediamine, 2-(2-hydroxyethoxy)-p-phenylenediamine, 2,5-diaminobiphenyl, 2-(2-thienyl)-p-phenylenediamine, 2-(3-thienyl)-p-phenylenediamine and 3-(2,5-diaminophenyl)pyridine.

3. The composition as defined in claim 1, wherein said 4,5-diamino-1H-pyrazole compounds are selected from the group consisting of 4,5-diamino-1-methyl-1H-pyrazole, 4,5- diamino-1-(2-hydroxyethyl)-1H-pyrazole, 4,5-diamino-1-(1-methylethyl)-1H-pyrazole, 4,5-diamino-1-(phenylmethyl)-1H-pyrazole, 4,5-diamino-1-[(4-methylphenyl)methyl]-1H-pyrazole, 4,5-diamino-1-(2-hydroxyethyl)-3-methyl-1H-pyrazole and 4,5-diamino-1-methyl-3-phenyl-1H-pyrazole.

4. The composition as defined in claim 1, wherein said p-aminophenol derivatives are selected from the group consisting of 3-methyl-p-aminophenol, 2-aminomethyl-p-aminophenol, 2-hydroxymethyl-p-aminophenol, 3-hydroxymethyl-p-aminophenol, 2-phenyl-p-aminophenol, 2-(2-thienyl)-p-aminophenol, 2-(3-thienyl)-p-aminophenol, 3-(2-thienyl)-p-aminophenol and 3-(3-thienyl)-p-aminophenol.

5. The composition as defined in claim 1, further comprising direct-dyeing dye compounds.

6. The composition as defined in claim 1, containing from 0.01 to 5 percent by weight of said 3-(2,4-diaminophenoxy)-1-propanol and from 0.01 to 5 percent by weight of said at least one developer compound.

7. The composition as defined in claim 6, further comprising at least one additional coupler and at least one additional developer compound.

8. The composition as defined in claim 1, having a pH of 6.8 to 11.5.

9. The composition as defined in claim 1, consisting of a hair dye composition.

10. A method for oxidative coloring of hair, said method comprising the steps of:
a) mixing a hair dye composition with an oxidant in order to form a ready-to-apply hair dyeing mixture;
b) applying the ready-to-apply hair dyeing mixture to the hair in an amount sufficient for the dyeing of the hair; and
c) leaving the ready-to-apply hair dyeing mixture applied in step b) on the hair for from 10 to 45 minutes at temperatures of from 15 to 50° C.; and then
d) optionally shampooing the hair, washing the hair with water, and then drying the hair;
wherein the hair dye composition comprises at least one developer compound and 3-(2,4-diaminophenoxy)-1-propanol, said 3-(2,4-diaminophenoxy)-1-propanol acting as a coupler;
wherein said at least one developer compound is selected from the group consisting of p-phenylenediamine derivatives of formula I:

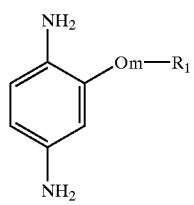

(I)

wherein m=0 or 1 and $R_1$ is a straight-chain $C_3$- to $C_6$-alkyl group, branched $C_3$- to $C_6$-alkyl group, a straight-chain $C_1$- to $C_6$-alkyl group, branched monohydroxy-$(C_1-C_6)$-alkyl group, a polyhydroxy-$(C_2-C_6)$-alkyl group, a straight-chain mono-$(C_2-C_6)$-alkoxy-$(C_2-C_6)$-alkyl group, branched mono-$(C_2-C_6)$-alkoxy-$(C_2-C_6)$-alkyl group, poly-$(C_2-C_6)$-alkoxy-$(C_2-C_6)$-alkyl group, a carbocyclic, heterocyclic, substituted or unsubstituted aromatic compound;

4,5-diamino-1H-pyrazole compounds of formula II:

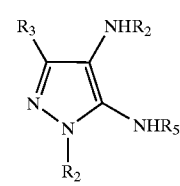

(II)

wherein $R_2$, $R_4$ and $R_5$, independently of each other, denote a hydrogen atom, a straight-chain $C_1$- to $C_6$-alkyl group branched $C_1$- to $C_6$-alkyl group, a straight-chain monohydroxy-$(C_1-C_6)$-alkyl group branched monohydroxy-$(C_1-C_6)$-alkyl group, a polyhydroxy-$(C_2-C_6)$-alkyl group, an unsubstituted benzyl group, a substituted benzyl group substituted on a benzene ring thereof, and $R_3$ denotes a straight-chain $C_1$- to $C_6$-alkyl group branched $C_1$- to $C_6$-alkyl group, a straight-chain monohydroxy-$(C_1-C_6)$-alkyl group branched monohydroxy-$(C_1-C_6)$-alkyl group, a polyhydroxy-$(C_2-C_6)$-alkyl group, a straight-chain mono-$(C_2-C_6)$-alkoxy-$(C_2-C_6)$-alkyl group branched mono-$(C_2-C_6)$-alkoxy-$(C_2-C_6)$-alkyl group, poly-$(C_2-C_6)$-alkoxy-$(C_2-C_6)$-alkyl group, a carbocyclic, heterocyclic, substituted aromatic compound, unsubstituted aromatic compound, or wherein $R_2$ denotes a methyl group, an isopropyl group, a 2-hydroxyethyl group, a benzyl group, or a 4-methylbenzyl group, when $R_3$, $R_4$ and $R_5$ are each said hydrogen atom; and p-aminophenol derivatives of formula III:

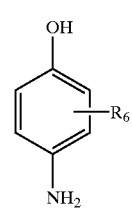

(III)

wherein $R_6$ is a straight-chain $C_1$- to $C_6$-alkyl group branched $C_1$- to $C_6$-alkyl group, a straight-chain monohydroxy-$(C1-C6)$-alkyl group branched monohydroxy-$(C_1-C_6)$-alkyl group, a polyhydroxy-$(C_2-C_6)$-alkyl group, a polyhydroxy-$(C_2-C_6)$-alkyl group, a straight-chain mono-$(C_2-C_6)$-alkoxy-$(C_2-C_6)$-alkyl group branched mono-$(C_2-C_6)$-alkoxy-$(C_2-C_6)$-alkyl group, poly-$(C_2-C_6)$-alkoxy-$(C_2-C_6)$-alkyl group, a carbocyclic, heterocyclic, substituted or unsubstituted aromatic compound.

11. The method as defined in claim 10, wherein said oxidant is a 6 percent by weight aqueous hydrogen peroxide solution, and said hair dye composition and said oxidant are mixed in a weight ratio of said hair dye composition to said oxidant of 5:1 and 1:2.

* * * * *